Figure 1:
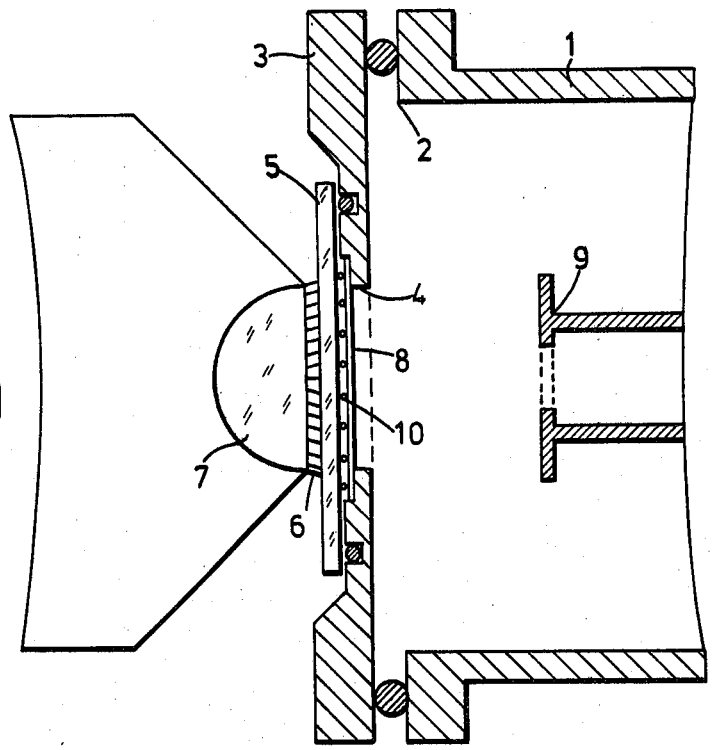

United States Patent [19]

Wechsung

[11] 4,296,322
[45] Oct. 20, 1981

[54] METHOD FOR ANALYZING ORGANIC SUBSTANCES

[75] Inventor: Reiner Wechsung, Cologne, Fed. Rep. of Germany

[73] Assignee: Leybold-Heraeus Gesellschaft mit beschränkter Haftung, Cologne, Fed. Rep. of Germany

[21] Appl. No.: 70,333

[22] Filed: Aug. 27, 1979

[30] Foreign Application Priority Data

Aug. 30, 1978 [DE] Fed. Rep. of Germany ....... 2837715

[51] Int. Cl.$^3$ ............................................ B01D 59/44
[52] U.S. Cl. .................................. 250/282; 250/287; 250/423 P
[58] Field of Search ............... 250/287, 288, 281, 282, 250/283, 423 R, 423 P; 73/61.1 C

[56] References Cited

U.S. PATENT DOCUMENTS

| 3,596,087 | 7/1971 | Health | 250/288 |
| 3,626,181 | 12/1971 | Wernlund | 250/282 |
| 4,158,775 | 6/1979 | Chutjlan et al. | 250/282 |
| 4,178,507 | 12/1979 | Brunnee et al. | 250/288 |

OTHER PUBLICATIONS

"Anal. Capabilities of Laser-Probe Mass Spect.", Kovalev et al., Int. J. of Mass Spect. and Ion Physics, 27, 1978, pp. 101-137.
"Laser Deportion-Mass Spect. of Polar Nonvolatile Bioorganic Mol.", Posthumus et al., Anal. Chem., vol. 50, No. 7, Jun. 1978, pp. 985-991.
"Stepwise Laser Photoionization of Molecules in a Mass Spect.: a new method for probing and detection of polyatomic molecules", Antonou et al., Optic Letters, vol. 3, No. 2, 8-78, pp. 37-39.

Primary Examiner—Bruce C. Anderson
Attorney, Agent, or Firm—Spencer & Kaye

[57] ABSTRACT

Organic substances, particularly those derived from a chromatograph, are analyzed by subjecting such a substance to laser radiation to produce negative ions of the substance, and by subjecting those negative ions to mass spectrometry, preferably time-of-flight mass spectrometry.

4 Claims, 2 Drawing Figures

U.S. Patent

Oct. 20, 1981

4,296,322

METHOD FOR ANALYZING ORGANIC SUBSTANCES

The analysis of organic substances presents particular difficulties because it is necessary to obtain information not only about the elements making up the molecules, but also about the structure of the molecules.

German Auslegeschrift [Published Patent Application] No. 2,654,057 discloses a procedure in which an eluate composed of a carrier liquid and an organic substance dissolved therein, upon exiting from a liquid chromatograph, is ionized, for example, by the application of a high intensity electric field, or by bombardment with ions, on a transporting belt or transporting wire and the resulting ions are examined with the aid of a mass spectrometer. This is intended to prevent premature destruction of the molecular structure, which occurs, for example, after evaporation and subsequent electron impact ionization of the substance to be examined.

Such a procedure required a solution of the substance being examined in the carrier liquid of the liquid chromatograph, i.e., it is unsuitable for the analysis of solid organic substances. Moreover, ionization by means of ion bombardment or by the application of an electric field causes a nonreproducible decomposition of the structure of the molecules so that it is difficult to draw a conclusion as to the starting substance from the resulting mass spectra, which essentially originate from molecule fragments, particularly since the number of the mass lines is multiplied due to multiple ionizations. Therefore, with increasing mass numbers of the molecules to be examined, the number of lines obtained increases to such an extent that the analysis of organic substances whose molecules have relatively high mass numbers (e.g. 200) is no longer possible.

It is the object of the present invention to provide a method for the analysis of organic substances which also permits the analysis of organic substances having particularly large molecules without increasing the difficulty of evaluating the resulting mass spectra as a result of multiple ionization.

This is accomplished according to the invention by using the mass spectroscopy of negative ions produced by laser beams for the analysis of the organic substances.

Surprisingly, organic substances can be analyzed particularly easily with this method, even if they have molecules with mass numbers of 1000 and more. This could initially not be expected because, in principle, it was assumed that organic molecules in particular would be destroyed to a particularly great extent by laser radiation. Although the mass spectra recorded with the aid of the method of the invention exhibit lines of fragments of molecules from the substance being examined, these lines are reproducible, i.e., they always originate from fragments which form special groups within the molecule structure. Thus these lines can also be used to provide information about the molecule structure.

A further advantage is the fact that in the analysis of organic substance according to the method of the invention there occur no, or only a negligibly small number of, doubly charged molecule ions so that unequivocal and reproducible results can be attained.

Figure 2:
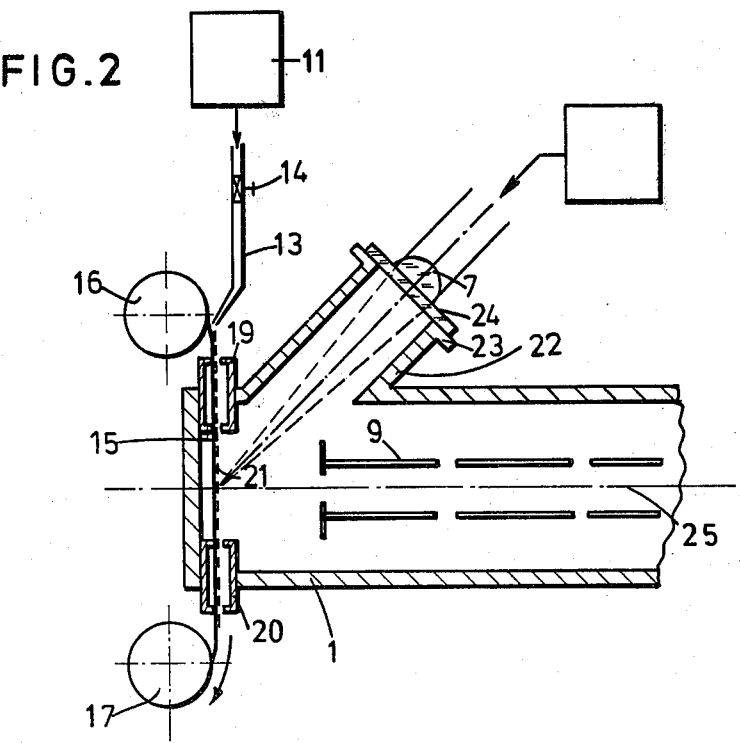

Further advantages and details of the invention will be explained with the aid of embodiments illustrated in FIGS. 1 and 2. It is shown in:

FIG. 1, a sectional view of an arrangement for practicing the analysis method of the invention with solid samples and FIG. 2, a sectional view of an arrangement for practicing the analysis method of the invention with liquid or gaseous samples.

The arrangement shown in FIG. 1 includes a housing 1, whose opening 2 is sealed in a vacuum-tight manner by covering flange 3. The covering flange 3 itself is likewise provided with an opening 4 which itself is sealed in a vacuum-tight manner by a covering glass 5.

Outside of the housing 1, the covering glass 5 is in contact with an optical focusing system for the laser radiation, represented here schematically by a concentrating lens 7, preferably via a layer 6 of immersion liquid. With the aid of this focusing system, the electromagnetic or laser radiation is focused in the area of the sample of solid organic material, indicated at 8, so that a small region of the sample is evaporated and ionized.

The ionized sample components with negative charge are sucked away by an electrode 9 disposed and maintained at positive potential with respect to the sample 8. From there these components travel into a mass spectrometer whose mass separation system may preferably be a time-of-flight tube. In order to have only sample 8, and not also the covering glass 5, evaporate, there is provided a spacer 10, e.g. a net, having a thickness of, for example, several tens of microns. The sample can also be held between two such nets.

The embodiment according to FIG. 2 can be used to analyze liquids as well as gases according to the teachings of the present invention. As an example, there is shown schematically a chromatograph 11 from which the substance to be examined, which is dissolved in a carrier fluid, enters into a conduit 13 including a metering valve 14.

In order to be able to introduce these fluids into the vacuum chamber 1, a transporting belt 15 is provided which in this embodiment has a finite length and unwinds from a reel 16 to be wound up on a reel 17. Locks 19 and 20 are provided for entrance and exit of the belt 15. The ionization of the substance layer (dashed line 21) applied to the transporting belt 15 is effected by means of laser light pulses. A connecting stud 22 with a connecting flange 23 is provided to the side of chamber 1 for introduction of the laser light. This connecting flange 23 is covered by a pane 24 which is transparent to laser light. Outside of this connecting stud there is provided a lens system 7 for focusing the laser light.

The lens system 7 and the plane of the window 24 are dimensioned and aligned in such a manner that the focal point of the laser light forms at the point where the axis 25 of the time-of-flight tube 9 intersects the transporting belt 15. With such a device it is thus possible to bombard the sample 21 with direct light. The negative ions produced thereby are sucked away in the manner described above in the direction toward the time-of-flight tube.

The above-described embodiment is particularly suitable for the analysis of liquid samples. However, gaseous samples can also be absorbed on belt 15 and thus introduced into the vacuum chamber 1. Moreover, there exists the further possibility of spraying the liquid or gaseous sample directly into the vacuum chamber in the area of the point of focus of the laser light. This can be effected, for example, discontinuously in synchronism with the laser light pulses.

It has been found to be particularly advantageous if the laser light has a wavelength of 265 nm and a pulse duration of 15 ns. In that case, a power density of about $10^9$ watt/cm$^2$ can be produced in the focal pont. The analyzed volume is about $10^{-12}$ cm$^3$.

I claim:

1. A method for analyzing high molecular weight organic substances exiting from a chromatograph comprising subjecting such substance to laser radiation to produce negative ions therefrom, and subjecting those negative ions to time-of-flight mass spectroscopy.

2. A method as defined in claim 1 wherein said step of subjecting such substance to laser radiation is carried out by delivering the substance from a chromatograph into a vacuum chamber, and focussing pulses of laser light from a laser onto the substance in the chamber to produce the negative ions, and said step of subjecting those negative ions to mass spectroscopy is carried out by disposing the time-of-flight tube of a time-of-flight mass spectrometer in the vacuum chamber and producing a positive potential with respect to the negative ions by means of an electrode disposed in the vacuum chamber at a location to attract the negative ions produced by the laser light into the time-of-flight tube.

3. A method as defined in claim 2 wherein said step of introducing the substance into the vacuum chamber is carried out conveying the substance on a transporting belt extending into the vacuum chamber.

4. A method as defined in claim 1 wherein the organic substances have mass numbers equal to or greater than 200.

* * * * *